(12) United States Patent
Liu et al.

(10) Patent No.: US 11,630,042 B2
(45) Date of Patent: Apr. 18, 2023

(54) HORIZONTAL JET-MECHANICAL COMBINED ROCK BREAKING TEST DEVICE AND METHOD

(71) Applicant: SHANDONG UNIVERSITY, Shandong (CN)

(72) Inventors: Bin Liu, Jinan (CN); Bo Zhang, Jinan (CN); Hongtao Zhu, Jinan (CN); Mengmeng Hu, Jinan (CN); Biao Li, Jinan (CN); Hanpeng Wang, Jinan (CN); Chunjin Lin, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 0 days.

(21) Appl. No.: 17/642,299

(22) PCT Filed: Jul. 13, 2020

(86) PCT No.: PCT/CN2020/101667
§ 371 (c)(1),
(2) Date: Mar. 11, 2022

(87) PCT Pub. No.: WO2021/212669
PCT Pub. Date: Oct. 28, 2021

(65) Prior Publication Data
US 2022/0341831 A1    Oct. 27, 2022

(30) Foreign Application Priority Data
Apr. 20, 2020  (CN) .......................... 202010312626.1

(51) Int. Cl.
*G01N 3/56* (2006.01)
*G01N 3/58* (2006.01)
*G01N 33/24* (2006.01)

(52) U.S. Cl.
CPC ............. *G01N 3/567* (2013.01); *G01N 33/24* (2013.01); *G01N 2203/0026* (2013.01); *G01N 2203/0067* (2013.01)

(58) Field of Classification Search
CPC .. G01N 3/00; G01N 3/02; G01N 3/56; G01N 3/567; G01N 3/58; G01N 33/24;
(Continued)

(56) References Cited

U.S. PATENT DOCUMENTS 6,349,595 B1    2/2002  Civolani et al.

FOREIGN PATENT DOCUMENTS

CN    101376543 A    3/2009
CN    102359919 A    2/2012
(Continued)

OTHER PUBLICATIONS

Jan. 28, 2021 Office Action issued in Chinese Patent Application No. 202010312626.1.
(Continued)

*Primary Examiner* — Nguyen Q. Ha
(74) *Attorney, Agent, or Firm* — Oliff PLC

(57) ABSTRACT

A horizontal jet-mechanical combined rock breaking test device and method. The device includes a horizontal base. One end of the horizontal base is provided with a multi-mode cutter head. A jet-mechanical combined cutter is provided on the multi-mode cutter head. The other end of the horizontal base is provided with a surrounding rock stress simulation bin for loading a rock sample. The multi-mode cutter head is connected to a driving mechanism, and the multi-mode cutter head is configured to advance and rotate horizontally along the horizontal base under the action of the driving mechanism, so that the jet-mechanical combined cutter is capable of acting on the rock sample.

14 Claims, 7 Drawing Sheets

(58) Field of Classification Search
CPC .. G01N 2203/0026; G01N 2203/0067; G01M 99/00
See application file for complete search history.

(56) References Cited

FOREIGN PATENT DOCUMENTS

| | | | | |
|---|---|---|---|---|
| CN | 103226068 A | 7/2013 | | |
| CN | 105736006 A | 7/2016 | | |
| CN | 106089225 A | 11/2016 | | |
| CN | 108535090 A | 9/2018 | | |
| CN | 109668754 A | 4/2019 | | |
| CN | 109779647 A | 5/2019 | | |
| CN | 110108588 A | 8/2019 | | |
| CN | 209416682 U | 9/2019 | | |
| CN | 110805447 A | 2/2020 | | |
| CN | 111076915 A * | 4/2020 | ............ | G01M 13/00 |
| DE | 198 10 511 A1 | 9/1999 | | |

OTHER PUBLICATIONS

Jan. 18, 2021 International Search Report issued in International Patent Application No. PCT/CN2020/101667.
Jan. 18, 2021 Written Opinion issued in International Patent Application No. PCT/CN2020/101667.
Fan Yang. "Development of a TBM Rock Breaking Test Equipment". Chinese Master's These Full-Text Database, Engineering Science & Technology II, No. 9, Sep. 15, 2018, pp. 15-17.

* cited by examiner

HORIZONTAL JET-MECHANICAL COMBINED ROCK BREAKING TEST DEVICE AND METHOD

TECHNICAL FIELD

The present disclosure belongs to the technical field of underground engineering tunneling, and specifically relates to a horizontal jet-mechanical combined rock breaking test device and method.

BACKGROUND

The description in this section merely provides background information related to the present disclosure and does not necessarily constitute the prior art.

With the continuous strengthening of infrastructure construction in China, the construction of headrace tunnel, road traffic and other tunnel projects is increasing year by year, and is developing towards long line, large buried depth and large section, which brings new challenges to tunnel construction. At present, compared with conventional drilling and blasting methods, TBM construction technology is widely used in tunnel construction because of its advantages in safety, cost-effectiveness, efficiency and the like. However, when applied in regions having hard rock with high abrasiveness and large buried depth, the tunneling efficiency of the TBM construction technology will be greatly reduced, which is manifested in decreased hob penetration, increased cutter wear, reduced bearing driving life, cutter head cracking and the like, thus seriously affecting the construction progress and increasing the tunneling cost.

In view of the shortcomings of TBM tunneling at present, in order to better achieve the goal of efficient rock breaking, combined rock breaking methods using a TBM cutter assisted by one or more technologies such as laser, water jet and microwave have been proposed. The theory and technology of water jet and TBM mechanical cutter combined rock breaking are relatively scarce. How to combine water jet with mechanical cutter and how to determine the parameters such as the quantities and relative positions of water jet nozzles and mechanical cutters are technical problems restricting the industrial application of jet-mechanical combined high-efficiency rock breaking. At present, there is a lack of a test device that can truly simulate TBM tunneling in the jet-mechanical rock breaking mode.

SUMMARY

In order to solve the above problems, the present disclosure provides a horizontal jet-mechanical combined rock breaking test device and method. The present disclosure adopts a horizontal structure and uses a multi-mode cutter head to advance and rotate along a horizontal direction and continuously cut rock. The rock can exert a three-directional confining pressure to restore a TBM rock breaking and tunneling process to the greatest extent. Using a multiple-degree-of-freedom jet-mechanical combined rock breaking cutter, the parameters such as a jet target distance, a jet angle, relative positions and quantity of jet nozzles and mechanical cutters can be adjusted, and a multi-mode jet-mechanical loading combination can be obtained, so as to carry out theoretical research of jet-mechanical combined rock breaking.

According to some embodiments, the following technical solutions are adopted in the present disclosure:

A horizontal jet-mechanical combined rock breaking test device includes a horizontal base, one end of the horizontal base is provided with a multi-mode cutter head, a jet-mechanical combined cutter is provided on the multi-mode cutter head, and the other end of the horizontal base is provided with a surrounding rock stress simulation bin for loading a rock sample;

the multi-mode cutter head is connected to a driving mechanism, and the multi-mode cutter head is configured to advance and rotate horizontally along the horizontal base under the action of the driving mechanism, so that the jet-mechanical combined cutter is capable of acting on the rock sample.

In the above technical solution, the base is a horizontal structure, and the multi-mode cutter head is used to advance and rotate along the horizontal direction and continuously cut rock, thus keeping the consistency with actual tunneling conditions and tunneling processes, and simulating the real scene of TBM tunneling to the greatest extent.

At the same time, the jet-mechanical combined cutter is provided on the multi-mode cutter head, which can be used for rock breaking research under different conditions.

As an alternative embodiment, the multi-mode cutter head includes a cutter head base, a high-pressure rotary joint, a diverter, the jet-mechanical combined cutter and a pipeline, the jet-mechanical combined cutter is provided on one side of the cutter head base, the high-pressure rotary joint is provided on the other side of the cutter head base, the high-pressure rotary joint is connected to the diverter, and the diverter is connected to a jet nozzle in each jet-mechanical combined cutter through the pipeline.

As an alternative embodiment, the jet-mechanical combined cutter includes a cutter holder, a mechanical cutter module and a jet cutter module are detachably provided on the cutter holder, and relative positions of the jet cutter module and the mechanical cutter module are adjustable.

As an alternative embodiment, a sliding rail is provided on the cutter holder, a sliding block is movably connected on the sliding rail, a jet cutter module is provided on the sliding block, a mechanical cutter module is provided in the middle of the cutter holder, and the mechanical cutter module includes a cutter body and a cutter rest.

As an alternative embodiment, the jet cutter module includes an adjustable support provided on the sliding block, a mechanical arm is rotatably provided on the adjustable support, a jet nozzle is provided on the mechanical arm, and the jet nozzle is capable of being connected to a hose connected to a jet liquid supply mechanism.

The jet-mechanical combined cutter further includes a measuring component, the measuring component includes a ranging sensor, a three-directional force sensor and a pressure monitoring sensor, the ranging sensor is provided on a cutter rest to monitor a distance between a hob and a target object, and the three-directional force sensor is provided on the cutter holder to monitor a stress on a rock breaking cutter in a process of breaking the target object, and the pressure sensor is provided between a jet nozzle and a jet liquid supply mechanism to monitor a jet output pressure.

As an alternative embodiment, the adjustable support includes a first connecting rod with a round rod and a second connecting rod with a round hole, the other end of the second connecting rod is connected to the sliding block, the adjustable support is parallel to the cutter rest, the first connecting rod and the second connecting rod are connected through the round rod and the round hole and are provided with a locking screw to realize an adjustable height and an adjustable angle between the first connecting rod and the second connecting rod, the jet mechanical arm is connected to the first connecting rod, and a distance between and orientations of the nozzle and the jet target are adjusted by adjusting attitudes of the jet mechanical arm and the adjustable support.

As an alternative embodiment, a cutter mounting mechanism and an adjusting mechanism are provided on the cutter head base of the multi-mode cutter head, a plurality of cutter holders are mounted on the cutter mounting mechanism, a distance between the cutter holders is adjusted through the adjusting mechanism, and a locking mechanism is provided on each cutter holder.

As an alternative embodiment, the horizontal base includes a reaction frame, the reaction frame includes a cross beam, a front reaction plate, a rear reaction plate, a bottom seat, advancement guide rails and a rock bin guide rail, where the cross beam and the bottom seat are arranged in parallel, upper and lower sides of the front reaction plate and the rear reaction plate are respectively connected to two ends of the cross beam and the bottom seat to form a frame structure, the advancement guide rails are provided on both the cross beam and the bottom seat to guide the multi-mode cutter head to move horizontally, and the rock bin guide rail is provided on the bottom seat and is slidably connected to the surrounding rock stress simulation bin.

As an alternative embodiment, the surrounding rock state simulation bin includes a bin body outer frame, pressurizing oil cylinders and a backing plate, the bin body outer frame provides reaction force for the pressurizing oil cylinders, and the pressurizing oil cylinders are provided in three directions of the bin body outer frame to apply a pressure to the backing plate which transfers the pressure to the rock sample to realize three-directional stress state simulation of the rock sample.

As an alternative embodiment, the driving mechanism includes advancement oil cylinders, a force transfer plate, a force transfer cylinder, a driving motor, a gearbox and a bearing, there are a plurality of advancement oil cylinders which are mounted on the rear reaction plate of the horizontal base, a piston rod of each advancement oil cylinder is hinged to the force transfer plate, an end portion of the force transfer plate is slidably connected to an advancement guide rail, the force transfer plate is fixedly connected to the force transfer cylinder, the driving motor and an outer race of the bearing are fixed to the force transfer cylinder, an inner race of the bearing is connected to the multi-mode cutter head, and the driving motor is connected to the inner race of the bearing through the gearbox.

A working method of the horizontal jet-mechanical combined rock breaking test device includes: adjusting relative positions and quantity of the jet nozzles and the mechanical cutters of the jet-mechanical combined cutter, a jet target distance or/and jet angle to form basic loading combinations of jet and mechanical cutters; adjusting mounting positions of multiple combined cutters with the same/different loading combinations on the multi-mode cutter head to form a cutter head with a specific loading mode and loading combination; and driving the multi-mode cutter head to move and rotate horizontally along the horizontal base, so that the jet-mechanical combined cutter is capable of acting on the rock sample in the surrounding rock stress simulation bin for a tunneling test.

Compared with the prior art, the present disclosure has the following beneficial effects:

The overall structure of the device provided by the present disclosure is a horizontal structure, so that rock breaking attitudes of the cutter head are the same as that of the real TBM, and rock breaking attitudes of the TBM and a loading environment of rock mass can be truly simulated. In addition, under the condition of horizontal structure, a rock cut surface is vertical, and cut rock slags fall off under the action of dead weight, which avoids the rock slags from being cut again and realizes the scheme that the cutter head continuously cuts the rock, which is the same as an actual rock breaking mode of TBM.

The present disclosure integrates the jet-mechanical combined cutter, the high-pressure rotary joint, the diverter and other components with the cutter head base to form the multi-mode cutter head, solves the problem of water jet transmission when the combined cutter rotates with the cutter head, and realizes the test scheme of cutter head active rotation for rock breaking, which is the same as an actual work of TBM. The guiding role of the test results is more effective.

The multi-mode cutter head provided in the present disclosure is provided with the cutter mounting mechanism, which fits with the jet-mechanical combined cutter. Through changes of the quantity and relative positions of the combined cutters and the multiple jet-mechanical combination modes provided by the combined cutter itself, the jet-mechanical rock breaking test of multiple modes and multiple loading combinations can be realized, which provides an effective test appliance for comprehensive study on jet rock breaking, mechanical rock breaking, and jet-mechanical combined rock breaking.

The multi-degree-of-freedom and detachable jet-mechanical combined cutter in the present disclosure integrates the mechanical cutter, the jet cutter and the measuring device, the jet cutter is omni-directionally adjustable around the mechanical cutter, and an incidence angle and a jet target distance of the jet nozzle are adjustable. Changing the relative positions of jet cutters and mechanical cutters can form a variety of loading combinations of jet cutters and mechanical cutters, which provides a basis for rock breaking of multiple modes and multiple loading combinations.

The jet cutter, the mechanical cutter and the measuring device in the present disclosure are detachable, which facilitates the switching between jet rock breaking, mechanical rock breaking and water jet-mechanical combined rock breaking. At the same time, it also lays a foundation for making full use of a cutter head space and forming a variety of rock breaking loading modes. The detachable measuring device is integrated on the combined cutter. When a mounting position of the combined cutter changes on the cutter head, the measuring device changes accordingly, without re-assembly and debugging, thus saving the test preparation time. At the same time, the detachable function of the measuring device facilitates maintenance, replacement and upgrading.

The combined cutter in the present disclosure is adapted to a working mode that the cutter head rotates to drive the cutter to break the rock. The mechanical cutter, the jet cutter and the measuring device are mounted on the cutter holder. When the cutter head rotates, relative positions of the mechanical cutter and the jet cutter on the cutter holder are fixed, and loading points on a surface of the target object do not change with the rotation of the cutter head, which provides necessary conditions for studying an optimal loading combination mode and so on. When the cutter head rotates, relative positions of the measuring device and the cutter are fixed, and measurement results are more effective. For example, when measuring penetration, if the relative positions of the measuring device and the cutter are not fixed, the measurement results are wrong.

The present disclosure considers the test conditions of a model machine, and is competent for the rock breaking test of the model machine under the cooperation with auxiliary devices, which not only expands the test scope of the present disclosure, but also provides test appliance support for promoting the industrial application of the jet-mechanical rock breaking mode.

The present disclosure has the advantages of reasonable overall structure, simple test method, high practicality and easiness in popularization.

BRIEF DESCRIPTION OF THE DRAWINGS

The accompanying drawings constituting a part of the present disclosure are used for providing further understanding for the present disclosure. Exemplary embodiments of the present disclosure and descriptions thereof are used for explaining the present disclosure and do not constitute an improper limitation to the present disclosure.

DETAILED DESCRIPTION

The present disclosure is further described below with reference to the accompanying drawings and embodiments.

It should be noted that the following detailed descriptions are all exemplary and are intended to provide a further understanding of the present disclosure. Unless otherwise specified, all technical and scientific terms used herein have the same meaning as commonly understood by a person of ordinary skill in the art to which the present disclosure belongs.

It should be noted that terms used herein are only for describing specific implementations and are not intended to limit exemplary implementations according to the present disclosure. As used herein, the singular form is intended to include the plural form, unless the context clearly indicates otherwise. In addition, it should further be understood that terms "comprise" and/or "include" used in this specification indicate that there are features, steps, operations, devices, components, and/or combinations thereof.

In the present disclosure, orientation or position relationships indicated by the terms such as "upper", "lower", "left", "right" "front", "rear", "vertical", "horizontal", "side", and "bottom" are based on orientation or position relationships shown in the accompanying drawings, and are merely relationship words that are determined for ease of describing the structural relationship between components or elements in the present disclosure, and are not intended to specifically refer to any component or element in the present disclosure. Therefore, such terms should not be construed as a limitation on the present disclosure.

In the present disclosure, terms such as "fixedly connected", "interconnection", and "connection" should be understood in a broad sense. The connection may be a fixed connection, an integral connection or a detachable connection; or the connection may be a direct connection, or an indirect connection by using an intermediary. Relevant scientific research or technical personnel in the art may determine the specific meanings of the foregoing terms in the present disclosure according to specific situations, and such terms should not be construed as a limitation on the present disclosure.

Figure 1:
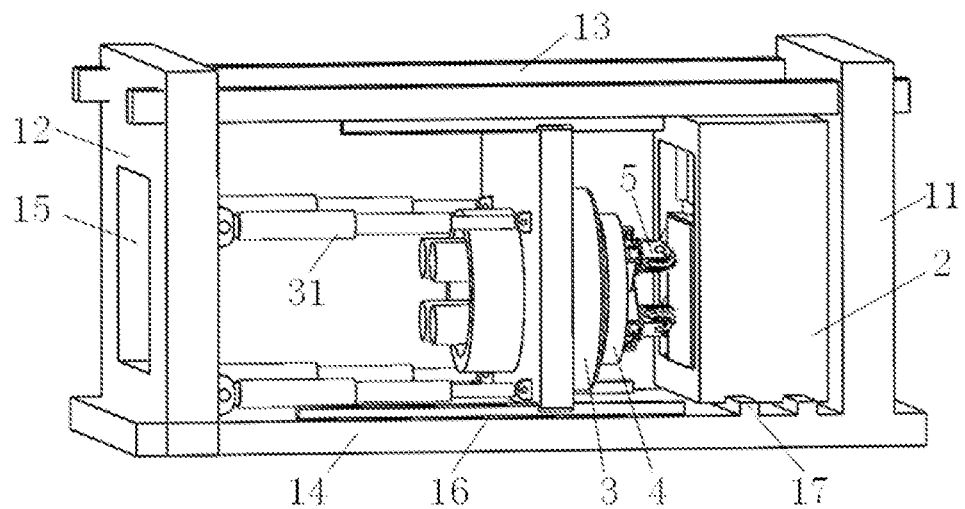
FIG. 1 illustrates a schematic view of an overall structure according to the present disclosure.

As shown in FIG. 1, a horizontal jet-mechanical combined rock breaking test device includes a reaction frame, a multi-mode cutter head 4 and a driving device 3 are provided on one side of the reaction frame, and the other side is provided with a surrounding rock stress simulation bin 2. Under the action of the driving device 3, the multi-mode cutter head 4 can move and rotate in a direction of the surrounding rock stress simulation bin 2, and then drive a jet-mechanical combined cutter 5 provided on the multi-mode cutter head 4 to cut a rock sample in the surrounding rock stress simulation bin for a rock breaking test.

The device can simulate an actual TBM tunneling process. The cutter head rotates and drives the mechanical cutter to cut the rock on a front tunnel excavation face, so as to study optimal cutter modes and parameters. The device can also be used as an actual tunneling tool to study the structural compatibility of tunneling tool, component wear and the like in during tunneling.

During the simulation, a surrounding rock state in a real engineering environment is simulated by pressurizing the rock through the surrounding rock stress simulation bin 2, and the driving device 3 provides a rotating force and an advancing force for the multi-mode cutter head 4, which can truly reproduce a tunneling process of a tunneling machine, and provide reliable test parameters for relevant theoretical research and engineering practice.

Figure 2:
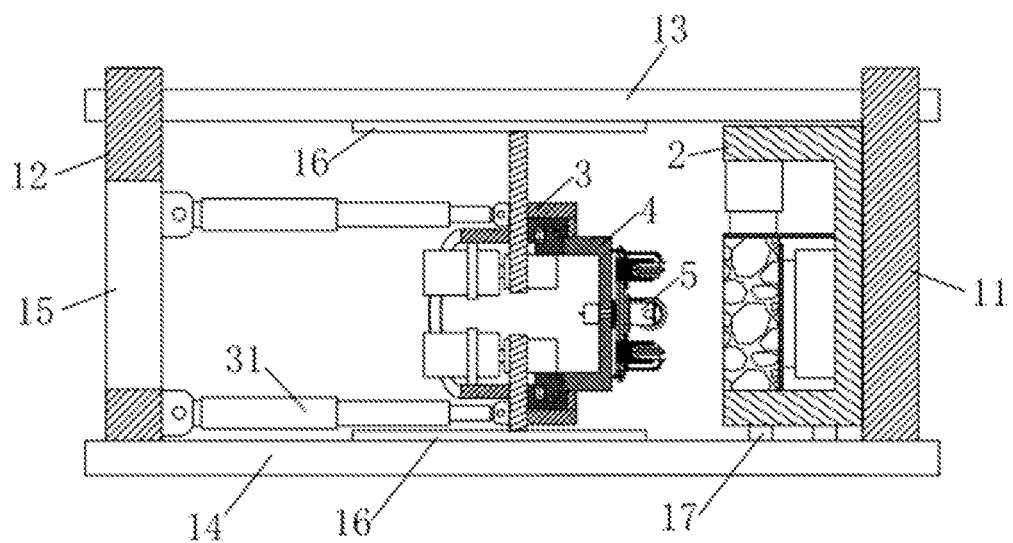
FIG. 2 illustrates a cross-sectional view of the overall structure according to the present disclosure.

Specifically, as shown in FIG. 2, the reaction frame includes a front reaction plate 11, a rear reaction plate 12, a cross beam 13, a bottom seat 14, an advancement guide rail 16 and a rock bin guide rail 17. The front reaction plate 11 and the rear reaction plate 12 are respectively provided at two ends of the bottom seat 14. In this embodiment, the front reaction plate 11 and the rear reaction plate 12 are parallel. At the same time, the cross beam 13 is provided between the front reaction plate 11 and the rear reaction plate 12, and the cross beam 13 is parallel to the bottom seat 14. As a whole, the reaction frame is a cuboid frame.

There are two groups of advancement guide rails 16, which are respectively disposed on the cross beam 13 and the bottom seat 14, and are slidably connected to a force transfer plate 32 of the driving device 3 to guide the straight (horizontal) advancement of the multi-mode cutter head 4. The rock bin guide rail 17 is disposed on the bottom seat and is slidably connected to the surrounding rock stress simulation bin 2 to guide the surrounding rock stress simulation bin 2 to move on the reaction frame to enter and exit the reaction frame for loading and unloading the rock sample.

An opening 15 is provided in the rear reaction plate 12 to help a model machine to enter and exit to carry out a model machine test.

Figure 4:
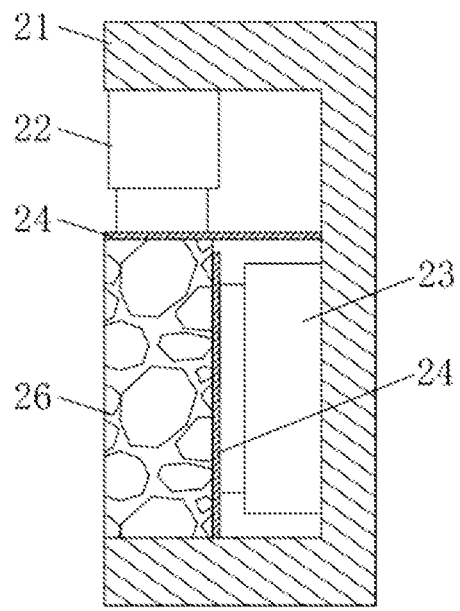
FIG. 4 illustrates a schematic cross-sectional structural view of a surrounding rock state simulation bin according to the present disclosure.
Figure 5:
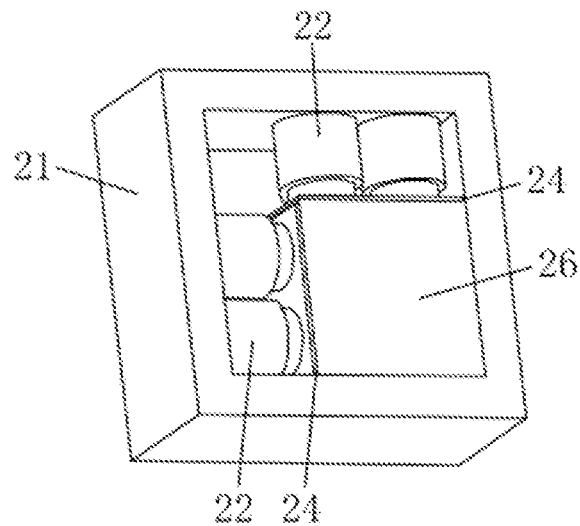
FIG. 5 illustrates a schematic view of an overall structure of a surrounding rock state simulation bin according to the present disclosure.

As shown in FIG. 4, the surrounding rock state simulation bin 2 includes a bin body outer frame 21, pressurizing oil cylinders 22, 23 and a backing plate 24. The bin body outer frame 21 provides a reaction force for the pressurizing oil cylinder 22. The pressurizing oil cylinders 22, 23 are provided in different directions (three directions in partial embodiments) of the bin body outer frame 21, as shown in FIG. 5, to apply a pressure to the corresponding backing plate 24 which transfers the pressure to a rock sample 26 to realize multi-directional stress state simulation of the rock sample. The surrounding rock state simulation bin with the rock sample is provided with reaction force by the front reaction plate 11 to balance an advancing force of the multi-mode cutter head 4.

Figure 3:
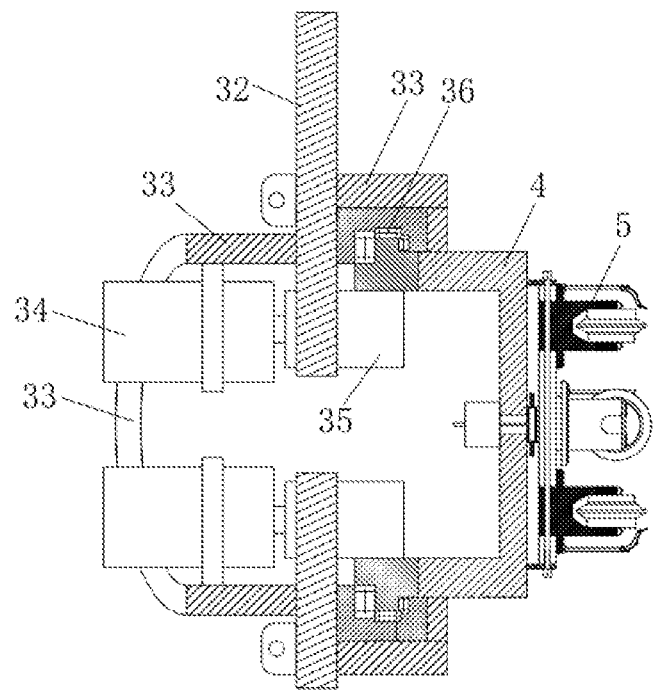
FIG. 3 illustrates a schematic partial cross-sectional structural view of a power device according to the present disclosure.

As shown in FIG. 2 and FIG. 3, the driving device 3 includes an advancement oil cylinder 31, a force transfer plate 32, a force transfer cylinder 33, a driving motor 34, a gearbox 35 and a bearing 36. In this embodiment, there are four advancement oil cylinders 31 (FIG. 2 is a side view, in which only two can be seen). The advancement oil cylinders 31 are hinged to four corners of the rear reaction plate 12, and piston rods of the advancement oil cylinders are hinged to the force transfer plate 32. Upper and lower sides of the force transfer plate 32 are slidably connected to the advancement guide rails 16 respectively. The force transfer plate 32 is fixedly connected to the force transfer cylinder 33. The driving motor 34 and an outer race of the bearing 36 are fixed to the force transfer cylinder 33. An inner race of the bearing 36 is fixedly connected to the multi-mode cutter head 4. The driving motor 34 drives the inner race of the bearing through the gearbox 35 to drive the cutter head to rotate. The advancement oil cylinder 31 drives the force transfer plate 32 to drive the whole cutter head to advance.

Figure 6:
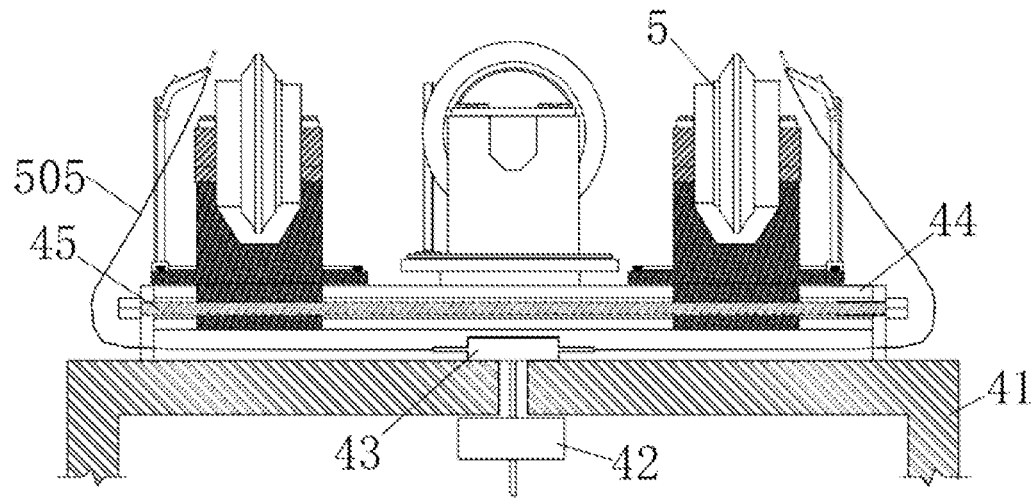
FIG. 6 illustrates a schematic cross-sectional structural view of a multi-mode cutter head according to the present disclosure.

As shown in FIG. 6, the multi-mode cutter head 4 includes a jet-mechanical combined cutter 5, a cutter head base 41, a high-pressure rotary joint 42, a diverter 43, a cutter mounting mechanism, an adjusting mechanism and a pipeline. A through hole is provided in the center of the cutter head base 41. The high-pressure rotary joint 42 and the diverter 43 are respectively located at two ends of the through hole. The high-pressure rotary joint 42 is connected to the diverter 43 through the pipeline provided in the through hole. The diverter 43 has a plurality of diverting branches. Each diverting branch is connected to a nozzle of a jet cutter through a high-pressure hose 505.

The cutting mounting mechanism may be implemented by using a multi-position mounting base plate, a cutter sliding rail, etc. The adjusting mechanism may be implemented by using a locking device, a lead screw, etc.

The high-pressure rotary joint 42 is provided on a back of the cutter head base 41, with one end connected to a jet pump set, and the other end connected to the diverter 43 located in the front of the cutter head base 41. The diverter 43 is structurally compatible with a cutter holder 509, the cutter mounting mechanism and the adjusting mechanism.

The diverter 43 includes a plurality of jet outlets. Each jet outlet is connected to a jet pipeline (forming a diverting branch) and connected to a jet nozzle 501. A valve is provided on the jet pipeline to control the opening and closing of jet. A pressure sensor is provided on a pipeline connecting the diverter and the jet nozzle.

Figure 7:
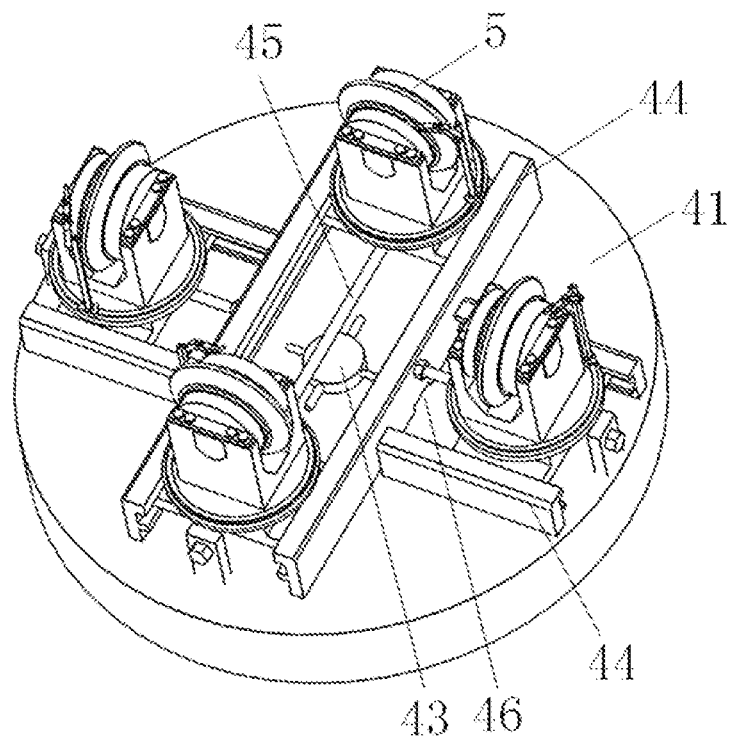
FIG. 7 illustrates a schematic view of an overall structure of a multi-mode cutter head according to the present disclosure.

In this embodiment, the cutter mounting mechanism is a cutter sliding rail 44, as shown in FIG. 7. In this embodiment, a plurality of groups of cutter sliding rails 44 are provided in the front of the cutter head base 41. In this example, there are 3 groups, one of which is a long sliding rail, and the other two of which are short sliding rails. The three groups of sliding rails form a cross-shaped arrangement.

In this embodiment, the adjusting mechanism is a lead screw 45 and the pipeline is a high-pressure hose 505.

The jet-mechanical combined cutter 5 includes the cutter holder 509. A detachable mechanical cutter and a jet cutter are mounted on the cutter holder. The jet cutter consists of the jet nozzle 501 and a nozzle adjusting device. The quantity of the mechanical cutters and the jet cutters is adjustable. Relative positions of the mechanical cutter and the jet cutter can be adjusted accordingly.

Figure 8:
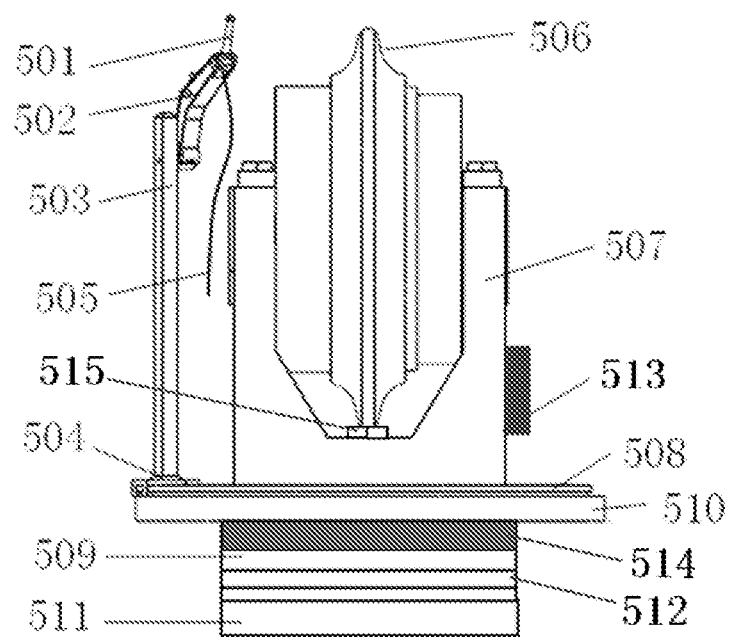
FIG. 8 illustrates a front view of a jet-mechanical combined cutter according to the present disclosure.
Figure 9:
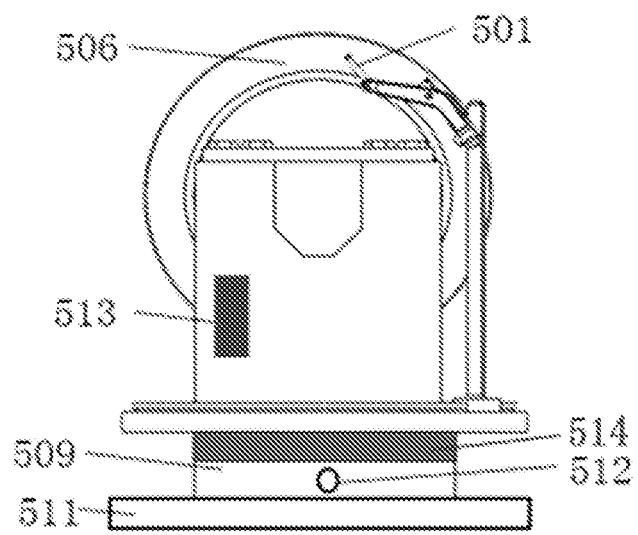
FIG. 9 illustrates a side view of the jet-mechanical combined cutter according to the present disclosure.

In this embodiment, as shown in FIG. 8, the jet-mechanical combined cutter includes the cutter holder 509. One three-dimensional force measuring device 514, one mechanical cutter and one jet cutter are mounted on the cutter holder. A lower end of the cutter holder protrudes outwards to form a cutter holder clamping plate 511.

An upper part of the three-dimensional force measuring device 514 is provided with a supporting platform 510. A circular sliding rail 508 is provided on the supporting platform. The mechanical cutter consists of a cutter body 506 and a cutter rest 507. The cutter rest 507 is connected to the supporting platform 510 or directly connected to the three-dimensional force measuring device 514 by a bolt 515. A ranging sensor 513 is mounted on a side of the cutter rest.

The jet cutter consists of the jet nozzle 501, a nozzle adjusting arm 502 and a jet support 503. The nozzle adjusting arm 502 is in fit and connection with the jet support 503 through a guide device. The jet nozzle 501 is also in fit and connection with the nozzle adjusting arm 502 through a guide device. A locking device is provided at each connection. A support clamping groove 504 is provided in the jet support 503, which is slidably connected to the circular sliding rail 508 on the supporting platform to realize circular motion of the jet cutter around the mechanical cutter. In this embodiment, one jet cutter is mounted on the circular sliding rail, a locking device is provided, and an edge of the sliding rail is provided with a positioning scale.

In other embodiments, the jet cutter module includes an adjustable support provided on a sliding block. A mechanical arm is rotatably provided on the adjustable support. A jet nozzle is provided on the mechanical arm. The jet nozzle is capable of being connected to a hose connected to a jet liquid supply mechanism.

The adjustable support includes a first connecting rod with a round rod and a second connecting rod with a round hole. The other end of the second connecting rod is connected to the sliding block. The adjustable support is parallel to the cutter rest. The first connecting rod and the second connecting rod are connected through the round rod and the round hole and are provided with a locking screw to realize an adjustable height and an adjustable angle between the first connecting rod and the second connecting rod. The jet mechanical arm is connected to the first connecting rod. The distance between and orientations of the nozzle and a jet target are adjusted by adjusting an attitude of the jet mechanical arm and the adjustable support.

In some embodiments, the position and attitude of the jet nozzle may be adjusted by using a multi-degree-of-freedom mechanical arm and a lifting rod.

The above different implementation structures are essentially to adjust the position and angle of the jet nozzle, change a jet target distance and relative positions of acting points of jet and the mechanical cutter on a target object, carry out the rock breaking test according to working conditions, and find optimal rock breaking modes and parameters.

Figure 10:
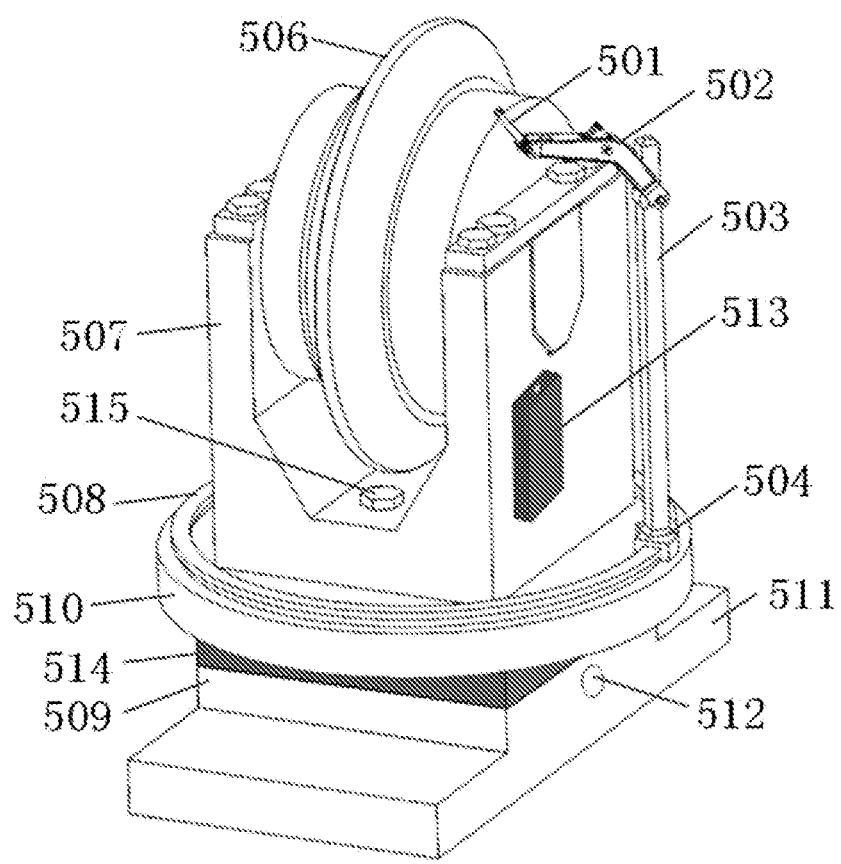
FIG. 10 illustrates a schematic three-dimensional structural view of a jet-mechanical combined cutter according to the present disclosure.

As shown in FIG. 10, a lower end of the cutter holder protrudes outwards to form the cutter holder clamping plate 511, which can be clamped in the cutter sliding rail 44 of the cutter head and move along the cutter sliding rail 44.

Of course, in other embodiments, the cutter holder clamping plate 511 may be an outward protrusion, or in other forms, as long as it can adapt to the cutter sliding rail 44 to ensure relative movement between them. For example, one component has a groove part and the other component has a clamping part matching the groove part.

Each group of cutter sliding rails 44 is equipped with a lead screw 45. A lead screw hole 512 is provided in each cutter holder 509. The lead screw fits with the lead screw hole to jointly adjust and lock the position of the cutter holder 509 on the cutter head base. In this embodiment, for the quantity of cutter holders mounted on the cutter sliding rails, two cutter holders are mounted on the long sliding rail and one cutter holder is mounted on the short sliding rail.

A gap is reserved between the cutter head base 41 and the combined cutter holder 509 for the high-pressure hose 505 to pass through. A hole is provided in the middle of the long sliding rail on the cutter head base 41 for the high-pressure hose to pass through. A circular hole is provided in the center of the cutter head base 41 as a jet pipeline passage. The high-pressure rotary joint 42 is provided on the back of the cutter head base, with one end connected to an external jet pump set, and the other end connected to the diverter 43 in the front of the cutter head base through the high-pressure hose. The diverter includes a plurality of jet outlets. Each jet outlet is connected to a high-pressure hose 505. The high-pressure hose either directly passes through a cavity between the cutter head base 41 and the cutter holder 509 along a direction of the long sliding rail, and is connected to a jet nozzle 501, or first passes through the hole 46 in the middle of the long sliding rail, and then passes through the cavity between the cutter head base 41 and the cutter holder 509 along a direction of the short sliding rail, and is connected to one jet nozzle. A valve is provided on the high-pressure hose to control the opening and closing of j et.

A pressure sensor is disposed on the high-pressure hose 505 connecting the diverter 43 and the jet nozzle 501.

In a test, the pressure sensor monitors a jet pressure in the test in real time, the ranging device monitors a penetration in a rock breaking process in real time, and the three-dimensional force measuring device monitors normal force, rolling force and lateral force data in the rock breaking process of a hob in real time, and transmits the collected data to a control system for data analysis and processing.

Figure 11:
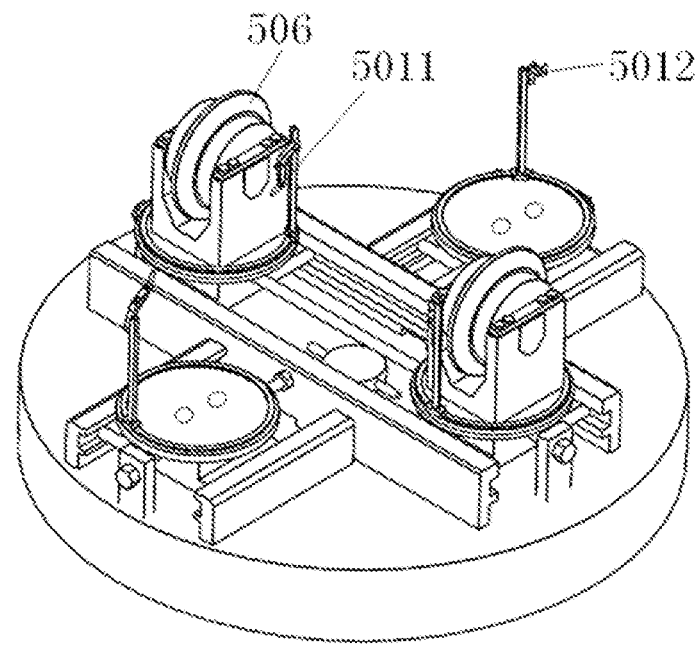
FIG. 11 illustrates a schematic view of a cutter combination in a jet-mechanical successive rock breaking test according to the present disclosure.

In some embodiments, in order to realize the rock breaking test under specific working conditions, the combined cutter holder 509 may only be provided with a mechanical cutter or jet cutter separately, or the jet cutter of the combined cutter may be closed for use the combined cutter as a mechanical cutter. As shown in FIG. 11, four groups of cutters are provided in total. Two groups are combined cutters with jet cutters closed, and the other two groups are jet cutters.

In this embodiment, the jet nozzle is a pure water continuous jet nozzle, and the cutter body of the mechanical cutter is the hob.

Of course, in other embodiments, the jet nozzle may be replaced with any one of a pulse water jet nozzle, an abrasive water jet nozzle, critical carbon dioxide and liquid nitrogen water jet nozzles, etc.

The cutter body of the mechanical cutter may also be replaced with a scraper.

In the test, the cutter head rotates and advances to drive the cutter to cut rock, forming many annular cutting trajectories on a rock surface, including cutting trajectories formed by the hob and the jet. A spacing between these cutting trajectories is a cutter spacing. Obviously, the cutter spacing includes a hob-hob spacing and a hob-jet cutter spacing. When either of the hob-hob spacing and the hob jet cutter spacing is 0, that is, the two cutting trajectories coincide, the rock breaking is referred to as identical-trajectory rock breaking, which can be further divided into hob-hob identical-trajectory rock breaking and hob jet identical-trajectory rock breaking. When neither of the hob-hob spacing and the hob-jet cutter spacing is 0, the rock breaking is referred to as different-trajectory rock breaking.

The cutter spacing is a key technical parameter in TBM tunneling, and is also an important aspect of jet-mechanical combined rock breaking. The position of the cutter holder on the multi-mode cutter head can be adjusted to realize the free adjustment of the cutter spacing, which provides a technical guarantee for the study on identical-trajectory and different-trajectory rock breaking under hob-hob and hob-jet combination conditions.

The present disclosure can carry out a variety of rock breaking tests, including the following test methods:

(1) Water jet of the jet-mechanical combined cutter 5 is closed (referring to FIG. 7 to FIG. 10), and a mechanical rock breaking test is carried out by using the hob 506 only. The jet cutter on the jet-mechanical combined cutter 5 may also be detached, and the mechanical rock breaking test is carried out by using the mechanical cutter only. The jet cutter and the supporting platform on the jet-mechanical combined cutter 5 may also be detached. The cutter rest of the mechanical cutter is directly mounted on the upper part of the three-dimensional force measuring device. The mechanical cutter is used for a mechanical rock breaking test. At this time, since the supporting platform is detached, a projection area of the cutter on the cutter head is smaller. On the one hand, a space of the sliding rail can be fully utilized. On the other hand, the hobs 506 of the two cutters on the long sliding rail may be closer to form a smaller cutter spacing and increase the rock breaking condition.

(2) The mechanical cutter of the jet-mechanical combined cutter 5 is detached (referring to FIG. 7 to FIG. 11), and a jet rock breaking test is carried out by using the water jet only. The jet nozzle 501 and the nozzle adjusting arm 502 may also be adjusted so that when the jet impacts on the target, the hob does not contact the target, and the combined cutter is used to carry out a jet rock breaking test.

(3) The water jet of the jet-mechanical combined cutter 5 is opened (referring to FIG. 7 to FIG. 10) to fit with the hob 506 to carry out a mechanical jet combined rock breaking test.

The above mechanical jet combined rock breaking test can be subdivided into the following test types:

(1) Jet-mechanical successive rock breaking: in the test, firstly, the water jet forms a damage area on the rock surface, such as cutting cracks and impact pits, and then the rock is cut by the hob. FIG. 11 illustrates a cutter combination implementation of such tests. The water jet of the jet-mechanical combined cutter on the long sliding rail is closed (corresponding to a jet nozzle 5011 in the figure) and the hob 506 is only used. At the same time, the hob of the jet-mechanical combined cutter on the short sliding rail is detached, and only the water jet is retained and used (corresponding to a jet nozzle 5012 in the figure) to carry out a jet-mechanical combined rock breaking test. In such tests, the acting point of the jet on the rock surface is far from the acting point of the hob, and a stress coupling effect can be ignored.

Figure 12:
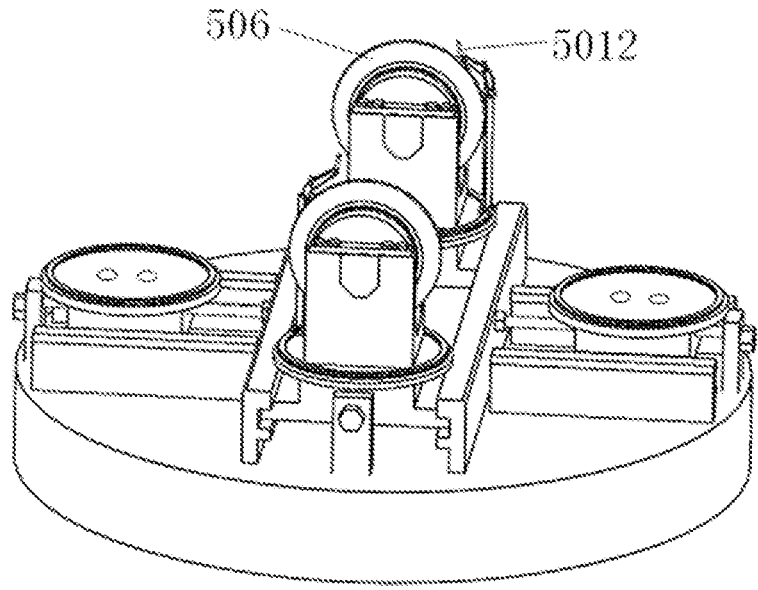
FIG. 12 illustrates a schematic view of a jet-mechanical joint rock breaking test according to the present disclosure.

(2) Jet-mechanical joint rock breaking: in the test, the acting point of the water jet on the rock surface is very close to the acting point of the hob, and an obvious stress coupling zone is formed in the rock to achieve the purpose of joint rock breaking. FIG. 12 illustrates a cutter combination implementation of such testes. The water jet on the same jet-mechanical combined cutter (corresponding to the jet nozzle 5012 in the figure) fits with the hob 506. The cutting acting points of the two on the rock surface are very close or coincide, forming an effective stress coupling effect.

In the above test methods, the identical-trajectory or different-trajectory rock breaking can be realized by adjusting the position of the cutter holder on the sliding rail, and a loading combination mode of the combined rock breaking cutter can be changed by adjusting an incident angle of the jet nozzle, a jet target distance, a relative position relationship between the jet nozzle and the hob and the like, so as to increase the diversity of rock breaking tests. In addition, the jet-mechanical successive rock breaking method and the jet-mechanical joint rock breaking method can also be jointly used.

Figure 13:
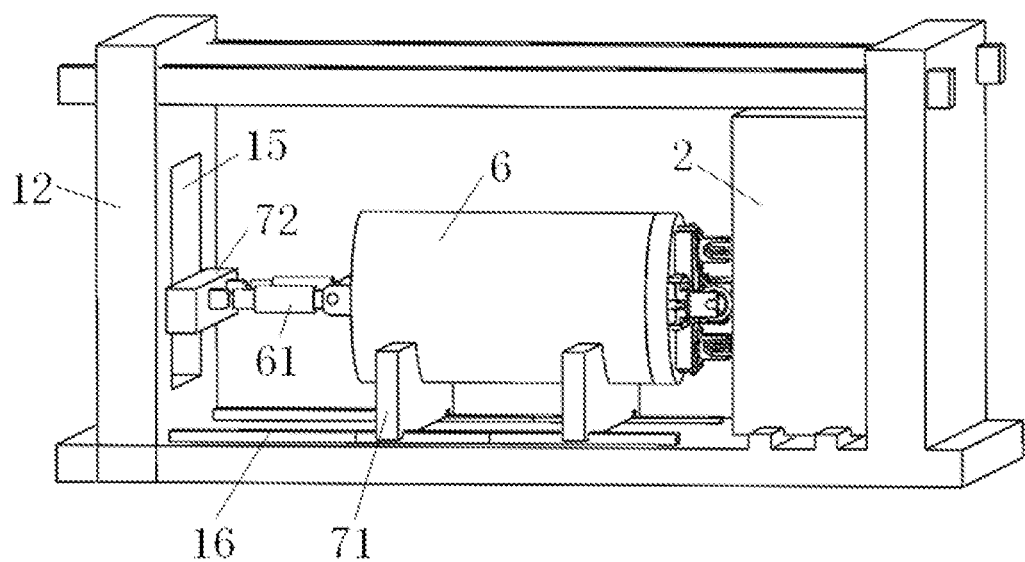
FIG. 13 illustrates an overall schematic view of a model machine in a rock breaking test according to the present disclosure.

In some embodiments, the rear reaction plate 12 of the reaction frame is provided with an opening 15, so as to allow TBM model machine tests, as shown in FIG. 13. During the test, firstly the driving device 3 and the multi-mode cutter head 4 are detached and a model machine supporting beam 71 is mounted on the advancement guide rail. Then, a model machine 6 enters the reaction frame from the opening 15 and is placed on the model machine supporting beam 71, and a model machine advancement reaction beam 72 is provided on the rear reaction plate 12 to provide a reaction force for model machine advancement. The model machine 6 fits with the surrounding rock state simulation bin 2 under the driving of the advancement oil cylinders 61 to carry out the model machine rock breaking test.

If the above model machine rock breaking test method is not adopted, the multifunctional cutter head 4 in the present device may be directly detached and replaced with a model machine cutter head to carry out a model machine cutter head test.

The jet-mechanical combined cutter is provided with a three-dimensional force measuring device and a ranging device. The combined cutter itself has multiple degrees of freedom. Through the adjustment between the jet support and the nozzle mechanical arm, the nozzle mechanical arm and the jet nozzle, and the jet cutter and the mechanical cutter, the jet cutter and the mechanical cutter can fit with each other to form a variety of specific loading combinations. For example, the jet nozzle is located in front, in rear or on one side of the hob, so as to carry out different combined loading on the rock, which increases the diversity of jet-mechanical rock breaking tests. When the jet cutter and the mechanical cutter fit with each other to form a specific loading combination, the specific loading combination can be adjusted by adjusting the position of the combined cutter on the sliding rail. In addition, it has an acquisition function for rock breaking data of the loading combination. The jet cutter and the mechanical cutter do not need to be recombined. The three-dimensional force measuring device and the ranging device do not need to be remounted, which greatly facilitates the development of jet-mechanical joint rock breaking tests. More specifically, the beneficial effects of adopting the jet-mechanical combined cutter scheme are as follows:

(1) The jet-mechanical combined cutter itself has multiple degrees of freedom. By adjusting the target distance, the jet angle, the relative positions and quantity of the jet nozzle and the mechanical cutter, a variety of jet-mechanical loading combinations can be formed, which is the basis of jet-mechanical multi-mode and multi-combination loading rock breaking.

(2) The modular scheme of the jet-mechanical combined cutter provides a prerequisite for simplifying a test preparation process and reducing test errors.

On the same combined cutter, the mechanical cutter and the jet cutter can form a variety of fits. Each fit corresponds to a combined cutter with a specific loading function, which is referred to as first-level loading combination. Multiple combined cutters can also form a variety of fits on the cutter head. Each fit corresponds to a cutter head with a loading function, which is referred to as second-level loading combination.

In the first-level loading combination, the free adjustment of the jet cutter and the mechanical cutter is solved through the nozzle adjusting device, forming basic combination of the jet and mechanical cutters, which lays a foundation for constructing a variety of loading cutter heads.

In the second-level combination, the combined cutter has original functions of its components. At the same time, the combined cutter integrates the mechanical cutter, the jet cutter and the measuring device on one cutter holder, and adjusting the position of the combined cutter on the cutter head can adjust basic combination of a specific loading function and the position of the measuring device on the cutter head, thus avoiding errors caused by the separate adjustment of the jet cutter and the mechanical cutter, avoiding the remounting and calibration of the measuring device, reducing the test preparation time and facilitating the test.

(3) The cutter body, the cutter rest, the supporting platform, the three-dimensional force measuring device, the ranging device, the jet nozzle, the nozzle adjusting arm and the jet support of the combined cutter are detachable, or some of the mechanisms/components are detachable, which creates convenient conditions for the switching between jet rock breaking, mechanical rock breaking and water jet-mechanical combined rock breaking.

In mechanical rock breaking and jet rock breaking tests, unnecessary components may be detached, which helps to reduce a volume of the cutter, make full use of the cutter head space, form more loading combinations, and avoid the damage to unnecessary components.

In the process of test or tunneling, if there are parts damaged, for example, if the jet nozzle is damaged, the jet nozzle can be replaced separately, thus reducing the cost of investment and facilitating the maintenance, replacement and upgrade.

Some parts of the combined cutter may be replaced with other parts to adjust the combination and form a modular test device.

(4) The use of the combined cutter reduces the complexity of cutter head and other parts, and is conducive to reducing errors of a test bed itself. For example, if the combined cutter is not used, in order to solve the free fitting between the mechanical cutter and the jet cutter and realize the test function of the present disclosure, it is necessary to increase the degree of freedom of the cutter head or cutter mounting mechanism, resulting in a more complex structure of the cutter head or cutter mounting mechanism, which is unfavorable to the rock breaking stiffness of hob groups and increases the test errors.

In the above embodiment, by adopting the horizontal structure, the multi-mode cutter head is used to advance and rotate along the horizontal direction and continuously cut the rock. The rock can exert a three-directional confining pressure to restore the TBM rock breaking and tunneling process to the greatest extent. The horizontal structure is adopted, so that a rock breaking attitude of the cutter head is the same as that of the real TBM, and the rock breaking attitude of the TBM and a loading environment of rock mass can be truly simulated. In addition, under the condition of horizontal structure, a rock cut surface is vertical, and the cut rock slags fall off under the action of dead weight, which avoids the rock slags from being cut again and realizes the scheme that the cutter head continuously cuts the rock.

The multi-mode cutter head is provided with the cutter mounting mechanism, which fits with the jet-mechanical combined cutter. Through changes of the quantity and relative positions of the combined cutters and the multiple jet-mechanical combination modes provided by the combined cutter itself, the jet-mechanical rock breaking test of multiple modes and multiple loading combinations can be realized.

Based on the jet-mechanical combined rock breaking cutter, the influence of a specific combination mode of the jet and mechanical cutters on the rock breaking efficiency and energy consumption can be studied.

At the same time, it also has a TBM model machine test function, which can serve the industrial application of jet-mechanical combined rock breaking technology.

The foregoing descriptions are exemplary embodiments of the present disclosure but are not intended to limit the present disclosure. The present disclosure may include various modifications and changes for a person skilled in the art. Any modification, equivalent replacement, or improvement made without departing from the spirit and principle of the present disclosure shall fall within the protection scope of the present disclosure.

The specific implementations of the present disclosure are described above with reference to the accompanying drawings, but are not intended to limit the protection scope of the present disclosure. A person skilled in the art should understand that various modifications or deformations may be made without creative efforts based on the technical solutions of the present disclosure, and such modifications or deformations shall fall within the protection scope of the present disclosure.

What is claimed is:

1. A horizontal jet-mechanical combined rock breaking test device, comprising: a reaction frame, wherein on the reaction frame is provided a multi-mode cutter head, plural jet-mechanical combined cutters are provided on the multi-mode cutter head, and on one end of the reaction frame is provided with a surrounding rock stress simulation bin for loading a rock sample; and the multi-mode cutter head is connected to a driving mechanism, and the multi-mode cutter head is configured to advance and rotate horizontally along the reaction frame under the action of the driving mechanism, so that the jet-mechanical combined cutters are capable of acting on the rock sample;

the multi-mode cutter head comprises a cutter head base, a high-pressure rotary joint, a diverter, the jet-mechanical combined cutter and a pipeline, wherein the jet-mechanical combined cutters are provided on one side of the cutter head base, the high-pressure rotary joint is provided on the other side of the cutter head base, the high-pressure rotary joint is connected to the diverter, and the diverter is connected to a jet nozzle in each jet-mechanical combined cutter through the pipeline;

the plural jet-mechanical combined cutters comprise a measuring component, the measuring component comprises a ranging sensor, and the ranging sensor is provided on a cutter rest to monitor a distance between a hob of the jet-mechanical combined cutter and a target object; and each of the jet-mechanical combined cutters comprises a cutter holder, a mechanical cutter module and a jet cutter module are detachably provided on the cutter holder, and relative positions of the jet cutter module and the mechanical cutter module are adjustable.

2. The horizontal jet-mechanical combined rock breaking test device according to claim 1, wherein each cutter holder is mounted on a mounting mechanism of the cutter head, a distance between cutter holders is adjusted through an adjusting mechanism, and a locking mechanism is provided on each cutter holder; and a sliding rail is provided on the cutter holder, a sliding block is movably connected on the sliding rail, a jet cutter module is provided on the sliding block, and a mechanical cutter module is provided in the middle of the cutter holder.

3. The horizontal jet-mechanical combined rock breaking test device according to claim 1, wherein the jet cutter module comprises an adjustable support provided on the sliding block, a mechanical arm is rotatably provided on the adjustable support, a jet nozzle is provided on the mechanical arm, and the jet nozzle is capable of being connected to a hose connected to a jet liquid supply mechanism.

4. The horizontal jet-mechanical combined rock breaking test device according to claim 1, wherein the measuring component further comprises a three-directional force sensor and a pressure monitoring sensor, the three-directional force sensor is provided on the cutter holder to monitor a stress on a rock breaking cutter in a process of breaking the target object, and the pressure sensor is provided between a jet nozzle and a jet liquid supply mechanism to monitor a jet output pressure.

5. The horizontal jet-mechanical combined rock breaking test device according to claim 1, wherein the surrounding rock stress simulation bin comprises a bin body outer frame, pressurizing oil cylinders and a backing plate, the bin body outer frame provides reaction force for the pressurizing oil cylinders, and the pressurizing oil cylinders are provided in three side surfaces of the bin body outer frame to apply a pressure to the backing plate which transfers the pressure to the rock sample to realize three-directional stress state simulation of the rock sample.

6. The horizontal jet-mechanical combined rock breaking test device according to claim 1, wherein the reaction frame comprises a cross beam, a front reaction plate, a rear reaction plate, a bottom seat, advancement guide rails and a rock bin guide rail, wherein the cross beam and the bottom seat are arranged in parallel, upper and lower sides of the front reaction plate and the rear reaction plate are respectively connected to two ends of the cross beam and the bottom seat to form a frame structure, the advancement guide rails are provided on both the cross beam and the bottom seat to guide the multi-mode cutter head to move horizontally, and the rock bin guide rail is provided on the bottom seat and is slidably connected to the surrounding rock stress simulation bin.

7. The horizontal jet-mechanical combined rock breaking test device according to claim 6, wherein the driving mechanism comprises advancement oil cylinders, a force transfer plate, a force transfer cylinder, a driving motor, a gearbox and a bearing, there are a plurality of advancement oil cylinders, which are mounted on the rear reaction plate of the reaction frame, a piston rod of each advancement oil cylinder is hinged to the force transfer plate, an end portion of the force transfer plate is slidably connected to an advancement guide rail, the force transfer plate is fixedly connected to the force transfer cylinder, the driving motor and an outer race of the bearing are fixed to the force transfer plate, an inner race of the bearing is connected to the multi-mode cutter head, and the driving motor is connected to the inner race of the bearing through the gearbox.

8. A working method of the horizontal jet-mechanical combined rock breaking test device according to claim 1, comprising: adjusting the relative positions and quantity of the jet nozzles and mechanical cutters of the jet-mechanical combined cutters, a jet target distance or/and jet angle to form basic loading combinations of jet and mechanical cutters; adjusting mounting positions of multiple combined cutters with the same/different loading combinations on the multi-mode cutter head to form a cutter head with a specific loading mode and loading combination; and driving the multi-mode cutter head to move and rotate horizontally along the reaction frame, so that the jet-mechanical combined cutters are capable of acting on the rock sample in the surrounding rock stress simulation bin for a tunneling test.

9. A working method of the horizontal jet-mechanical combined rock breaking test device according to claim 2, comprising: adjusting the relative positions and quantity of the jet nozzles and mechanical cutters of the jet-mechanical combined cutters, a jet target distance or/and jet angle to form basic loading combinations of jet and mechanical cutters; adjusting mounting positions of multiple combined cutters with the same/different loading combinations on the multi-mode cutter head to form a cutter head with a specific loading mode and loading combination; and driving the multi-mode cutter head to move and rotate horizontally along the reaction frame, so that the jet-mechanical combined cutters are capable of acting on the rock sample in the surrounding rock stress simulation bin for a tunneling test.

10. A working method of the horizontal jet-mechanical combined rock breaking test device according to claim 3, comprising: adjusting the relative positions and quantity of the jet nozzles and mechanical cutters of the jet-mechanical combined cutters, a jet target distance or/and jet angle to form basic loading combinations of jet and mechanical cutters; adjusting mounting positions of multiple combined cutters with the same/different loading combinations on the multi-mode cutter head to form a cutter head with a specific loading mode and loading combination; and driving the multi-mode cutter head to move and rotate horizontally along the reaction frame, so that the jet-mechanical combined cutters are capable of acting on the rock sample in the surrounding rock stress simulation bin for a tunneling test.

11. A working method of the horizontal jet-mechanical combined rock breaking test device according to claim 4, comprising: adjusting the relative positions and quantity of the jet nozzles and the mechanical cutters of the jet-mechanical combined cutters, a jet target distance or/and jet angle to form basic loading combinations of jet and mechanical cutters; adjusting mounting positions of multiple combined cutters with the same/different loading combinations on the multi-mode cutter head to form a cutter head with a specific loading mode and loading combination; and driving the multi-mode cutter head to move and rotate horizontally along the reaction frame, so that the jet-mechanical combined cutters are capable of acting on the rock sample in the surrounding rock stress simulation bin for a tunneling test.

12. A working method of the horizontal jet-mechanical combined rock breaking test device according to claim 6, comprising: adjusting the relative positions and quantity of the jet nozzles and mechanical cutters of the jet-mechanical combined cutters, a jet target distance or/and jet angle to form basic loading combinations of jet and mechanical cutters; adjusting mounting positions of multiple combined cutters with the same/different loading combinations on the multi-mode cutter head to form a cutter head with a specific loading mode and loading combination; and driving the multi-mode cutter head to move and rotate horizontally along the reaction frame, so that the jet-mechanical combined cutters are capable of acting on the rock sample in the surrounding rock stress simulation bin for a tunneling test.

13. A working method of the horizontal jet-mechanical combined rock breaking test device according to claim 5, comprising: adjusting the relative positions and quantity of the jet nozzles and mechanical cutters of the jet-mechanical combined cutters, a jet target distance or/and jet angle to form basic loading combinations of jet and mechanical cutters; adjusting mounting positions of multiple combined cutters with the same/different loading combinations on the multi-mode cutter head to form a cutter head with a specific loading mode and loading combination; and driving the multi-mode cutter head to move and rotate horizontally along the reaction frame, so that the jet-mechanical combined cutters are capable of acting on the rock sample in the surrounding rock stress simulation bin for a tunneling test.

14. A working method of the horizontal jet-mechanical combined rock breaking test device according to claim 7, comprising: adjusting the relative positions and quantity of the jet nozzles and mechanical cutters of the jet-mechanical combined cutters, a jet target distance or/and jet angle to form basic loading combinations of jet and mechanical cutters; adjusting mounting positions of multiple combined cutters with the same/different loading combinations on the multi-mode cutter head to form a cutter head with a specific loading mode and loading combination; and driving the multi-mode cutter head to move and rotate horizontally along the reaction frame, so that the jet-mechanical combined cutters are capable of acting on the rock sample in the surrounding rock stress simulation bin for a tunneling test.

\* \* \* \* \*